(12) United States Patent
Ko

(10) Patent No.: US 7,824,610 B2
(45) Date of Patent: Nov. 2, 2010

(54) PLASMA TREATMENT MODULE-EQUIPPED STERILIZATION APPARATUS AND STERILIZATION METHOD

(75) Inventor: Jung-Suek Ko, Seoul (KR)

(73) Assignee: Human Meditek Co., Ltd., Seoul (KR)

( * ) Notice: Subject to any disclaimer, the term of this patent is extended or adjusted under 35 U.S.C. 154(b) by 1959 days.

(21) Appl. No.: 10/637,752

(22) Filed: Aug. 8, 2003

(65) Prior Publication Data
US 2004/0120869 A1 Jun. 24, 2004

(30) Foreign Application Priority Data
Nov. 8, 2002 (KR) ............ 10-2002-0069082
Apr. 10, 2003 (KR) ............ 10-2003-0022735

(51) Int. Cl.
*A61L 2/14* (2006.01)
(52) U.S. Cl. ............ 422/30; 422/186.05; 422/292
(58) Field of Classification Search ............ None
See application file for complete search history.

(56) References Cited

U.S. PATENT DOCUMENTS 4,643,876 A * 2/1987 Jacobs et al. ............ 422/23
5,872,359 A * 2/1999 Stewart et al. ............ 250/339.12
6,077,480 A * 6/2000 Edwards et al. ............ 422/28

FOREIGN PATENT DOCUMENTS

| KR | 1997-0010057 | 6/1997 |
|---|---|---|
| KR | 10-035014 | 1/2003 |

* cited by examiner

*Primary Examiner*—Elizabeth L McKane
(74) *Attorney, Agent, or Firm*—The Webb Law Firm

(57) ABSTRACT

Disclosed is a plasma treatment module-equipped sterilization apparatus which can easily sterilize thin, long lumens without the aid of boosters. The sterilization apparatus comprises a sterilization chamber, a sterilizing agent feeding line, hydrogen peroxide solution acting as a sterilizing agent, an injection heater, a mass flow controller, a vacuum pump, and an exhaust line. A plasma treatment module is provided on the exhaust line to decompose the hydrogen peroxide vapor exhausted from the sterilization chamber with plasma. Also, disclosed is the sterilization method using the plasma treatment module-equipped sterilization apparatus.

6 Claims, 1 Drawing Sheet

PLASMA TREATMENT MODULE-EQUIPPED STERILIZATION APPARATUS AND STERILIZATION METHOD

TECHNICAL FIELD

The present invention relates, in general, to a sterilization apparatus and, more particularly, to a sterilization apparatus, which utilizes hydrogen peroxide vapor as a sterilizing agent, and is equipped with a plasma treatment module. The plasma treatment module is provided on the evacuating line, attracts hydrogen peroxide vapor and decomposes the vapor into hydrogen, oxygen and water, all of which are non-toxic and environmentally friendly, by using the high density plasma, to avoid direct exhaustion of the vapor out of the reaction chamber into the air. Also, the present invention is concerned with a sterilization method using the plasma treatment module-equipped sterilization apparatus.

BACKGROUND ART

Nowadays, hydrogen peroxide plasma is widely utilized to kill microorganisms living on various types of articles to be sterilized (hereinafter referred to as "sterilization objects"), including disposable or recycled medical instruments. Many techniques are now suggested with regard to the sterilization process utilizing the hydrogen peroxide plasma. In order to better understand the background of the invention, a description about some of the prior arts will be given below.

Korean Pat. No. 0132233 discloses a sterilization method comprising the steps of bringing the sterilization objects into contact with a hydrogen peroxide solution, introducing into a reaction chamber the sterilization objects which retains residual hydrogen peroxide, producing active species from the residual hydrogen peroxide on the sterilizing objects by generating plasma around the sterilization objects in the reaction chamber, and holding the sterilization objects in the plasma for 5 to 50 min that is enough to allow the active species to kill the microorganisms.

Also, disclosed is a removing method of the remaining hydrogen peroxide from the sterilized objects, which comprises a step of generating plasma around the sterilized objects in a reaction chamber to decompose the remaining hydrogen peroxide into non-toxic compounds.

This plasma sterilization method, however, has disadvantages. In the sterilization method, direct contact between the sterilization objects and plasma occurs, causing polymer-based medical devices to undergo changes of physical and chemical properties, e.g., color changes or material hardening. Additionally, when the total volume of the sterilization objects is over 70% of the volume of the reaction chamber, some of them are highly apt to remain incompletely sterilized.

Furthermore, the reaction chamber of the prior art is greatly limited in size because plasma must be uniformly generated in the reaction chamber. Another drawback of the method is that sterilization objects near the cathode are not sterilized because largely extending cathode sheath zone is formed near the cathode due to a self-bias, which is usually induced in a capacitively-coupled plasma.

In Korean Pat. Laid-Open Publication No. 1995-003116, a sterilization method is disclosed, which comprises the steps of introducing the sterilization objects into a reaction chamber and bringing the sterilization objects into contact with the hydrogen peroxide vapor released from an organic complex of hydrogen peroxide, which is substantially non-aqueous, to sterilize the objects.

In addition, another sterilization method is further disclosed in the Laid-Open Publication No. 1995-003116, which comprises the steps of introducing the sterilization objects into a reaction chamber, bringing the sterilization objects into contact with the hydrogen peroxide vapor released from an organic complex of hydrogen peroxide, which is substantially non-aqueous, to sterilize the objects, generating plasma at a distance from the sterilization objects, providing the plasma to the objects, and holding the objects in the plasma.

In the former sterilization method of the Laid-Open Publication No. 1995-003116, sterilization simply resorts to the contact of sterilization objects with hydrogen peroxide vapor. The latter sterilization method of the Laid-Open Publication No. 1995-003116 is characterized by the sterilization process conducted by the chemical reaction of microorganisms with active species formed from the hydrogen peroxide plasma, in addition to the primary sterilization process based on the simple contact with hydrogen peroxide vapor.

However, the methods of the prior arts show serious problems. In the former sterilization method of the Laid-Open Publication No. 1995-31116, the hydrogen peroxide vapor is released into the air, producing environmental pollution and bringing about respiratory disorders to the user.

In the latter sterilization method of the Laid-Open Publication No. 1995-31116 and the sterilization method of the Korean Pat. No. 0132233, the sterilization objects exposed to the hydrogen peroxide vapor or solution are kept in plasma in order for active species formed from the plasma to conduct their germicidal function. Thus, a part of the hydrogen peroxide can be decomposed during the step of holding the objects in the plasma. However, when many sterilization objects are treated at the same time in the chamber, hydrogen peroxide is not completely decomposed into oxygen, hydrogen and water. Thus, the hydrogen peroxide, which remains intact, is released into the air, producing environmental pollution and bringing about respiratory disorders to the user.

Since all sterilization methods of the prior arts described above are carried out in vacuum states at the hydrogen peroxide vapor plasma of low pressure, which plays a crucial role in the sterilization process, so weakly penetrates into thin, long lumens, e.g., flexible endoscopes $\phi$ 1 mm or less in diameter with a length of 50 cm or longer, that sterilization is not perfectly achieved in them. To sterilize such a lumen, hydrogen peroxide vapor is injected through boosters, which are attached to each end of the lumen.

DISCLOSURE OF THE INVENTION

Accordingly, the present invention has been made keeping in mind the above problems occurring in the prior art, and an object of the present invention is to provide a plasma treatment module-equipped sterilization apparatus and method, which attracts hydrogen peroxide vapor as a sterilizing agent to kill microorganisms present on the articles, such as medical instruments and tools, and decomposes the vapor into hydrogen, oxygen and water, all of which are non-toxic and environmentally friendly, in a plasma treatment module, instead of releasing directly the exhaust vapor out of the reaction chamber into the air.

Another object of the present invention is to provide a plasma treatment module-equipped sterilization apparatus and method, in which a sterilization chamber is filled with hydrogen peroxide vapor at pressure higher than atmospheric pressure, thereby easily sterilizing thin, long lumens, such as endoscopes with diameter of 1 mm or less and length of 50 cm or greater, without the aid of a booster.

In order to accomplish the above object, the present invention provides a plasma treatment module-equipped sterilization apparatus, comprising: a sterilization chamber for receiving therein sterilization objects; a sterilizing agent feeding line, interconnected with the sterilization chamber, comprising a hydrogen peroxide solution, acting as a sterilizing agent, an injection heater for vaporizing the sterilizing agent by heating, and a mass flow controller for controlling the injection amount of the vaporized hydrogen peroxide; and a vacuum pump, connected to the sterilization chamber via an exhaust line, for extracting air from the sterilization chamber to form a vacuum state, wherein a plasma treatment module is provided on the exhaust line to treat the vapor from the sterilization chamber by using a high density plasma.

In accordance with an embodiment, the plasma treatment module comprises two electrodes, facing each other, as a cathode and an anode therein, and is connected to a plasma generator composed of a high frequency power source, an impedance matching controller and an impedance matching circuit. The plasma generator may be based on a radio frequency discharge of capacitively coupled or inductively coiled type. In addition, the plasma generator may be based on an arc discharge utilizing high voltage direct current or on a corona discharge utilizing high voltage alternating current.

Also, the present invention provides a sterilization method utilizing the plasma treatment module-equipped apparatus, comprising the steps of: introducing sterilization objects into a sterilization chamber and closing the chamber; forming a desired pressure in the sterilization chamber by use of the vacuum pump, injecting hydrogen peroxide vapor into the sterilization chamber to a desired reaction pressure and keeping the sterilization objects in the hydrogen peroxide vapor for a desired period of time to achieve sterilization; and exhausting the hydrogen peroxide vapor from the sterilization chamber by means of the vacuum pump and decomposing the vapor from the reaction chamber into oxygen, hydrogen and water in the plasma treatment module before releasing the vapor into the air.

In accordance with another embodiment, the hydrogen peroxide vapor is injected into the sterilization chamber at a pressure higher than the atmospheric pressure.

BRIEF DESCRIPTION OF THE DRAWINGS

The above and other objects, features and advantages of the present invention will be more clearly understood from the following detailed description taken in conjunction with the accompanying drawing, in which.

BEST MODE FOR CARRYING OUT THE INVENTION

Figure 1:
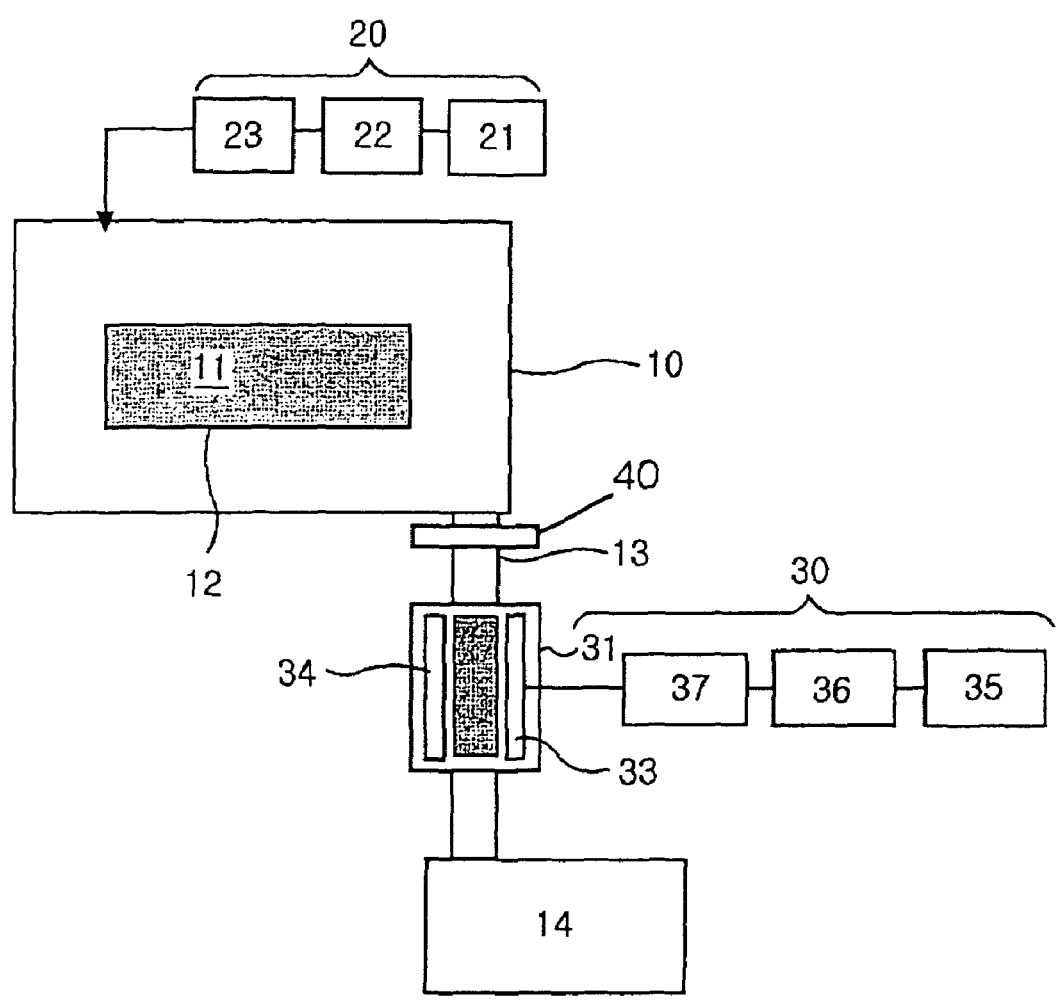
FIG. 1 is a schematic diagram showing the structure of the plasma treatment module-equipped sterilization apparatus of the present invention.

The application of the preferred embodiments of the present invention is best understood with reference to the accompanying drawing.

FIG. 1 schematically shows the structure of a plasma treatment module-equipped sterilization apparatus according to the present invention. As shown in the drawing, the sterilization apparatus of the present invention comprises a reaction chamber 10 for receiving therein sterilization objects 11, such as medical instruments, e.g., surgical tools. Before being introduced into the chamber 10, the sterilization objects 11 are preferably wrapped with a wrapping material 12. Connected via an exhaust line 13 to a lower part of the sterilization chamber 10, a vacuum pump 14 is provided to exhaust air from the sterilization chamber 10 to form a vacuum state.

To the sterilization chamber 10 is provided a sterilizing agent feeding line 20 which comprises a sterilizing agent, that is, hydrogen peroxide solution 21, an injection heater 22 for vaporizing the sterilizing agent by heating and for injecting the hydrogen peroxide vapor into the sterilization chamber 10, and a mass flow controller 23 for controlling the injection amount of the vaporized hydrogen peroxide.

At the mid site of the exhaust line 13, a plasma treatment module 31 is provided in which the vapor (hydrogen peroxide) reacts with the plasma. The plasma treatment module 31 comprises a plasma generator 30, which may be based on a radio frequency discharge of capacitively-coupled or inductively-coiled type. In addition, the plasma generator 30 may be based on an arc discharge utilizing high voltage direct currents or on a corona discharge utilizing high voltage alternating currents.

In accordance with an embodiment of the present invention, the plasma generator 30 is of a radio frequency discharge. In the plasma treatment module 31 on the exhaust line 13, a cathode 33 and an anode 34 are provided, facing each other. A radio frequency source (RF Power Generator) 35, which supplies frequencies suitable to generate plasma in an optimal condition, is electrically connected to the cathode 33 through both an impedance matching controller 36 and an impedance matching circuit 37.

In the plasma treatment module 31, the two electrodes are in close proximity to each other at an interval of 0.5-40 cm to easily generate high density plasma even with a small capacity power source.

The frequency of the high frequency power source 35 may fall into a variety of frequency bands. AS the frequency is higher, the higher density plasma is generated. However, the higher frequency generator requires more expensive equipment and additional equipment capable of shielding electromagnetic radiation. Therefore, it is preferable to select a frequency band suitable to equipment in practical use.

To control the internal pressure of both the sterilization chamber 10 and the plasma treatment module 31, an automatic pressure control valve 40 is installed on the exhaust line 13 between the sterilization chamber 10 and the plasma treatment module 31.

A description will be given of the sterilization method using the plasma treatment module-equipped sterilization apparatus of the invention, below, in one aspect of the present invention.

Sterilization objects 11, e.g., a medical instrument or a surgical tool, is wrapped in the wrapping material 12, and placed into the sterilization chamber 10, and the door of the sterilization chamber 10 is closed. After opening the automatic pressure control valve 40, the vacuum pump 14 is operated to exhaust air from the sterilization chamber 10 and the plasma treatment module 31 to the extent that a desired level of vacuum is formed.

When the vacuum pump 14 creates a desired level of vacuum inside the sterilization chamber 10 and the plasma treatment module 31, the automatic pressure control valve 40 located on the exhaust line 13 is closed. After which, the hydrogen peroxide vapor formed from the hydrogen peroxide solution 21 by the injection heater 22 is injected into the sterilization chamber 10 via the mass flow controller 23. In this regard, the pressure of the sterilization chamber 10 falls into the range of $(1.36~13.6) \times 10^3$ kgf/cm².

After being formed inside the sterilization chamber 10, a desired pressure of hydrogen peroxide vapor is maintained for a predetermined period of time to achieve perfect sterilization. Although being dependent on the concentration of the hydrogen peroxide vapor, the sterilization time is preferably long enough to kill all microorganisms existing on the sterilization objects. As for the wrapping material 12, anything is acceptable if it possesses a fiber-like structure capable of allowing ventilation of the plasma therethrough, because it is simply used to wrap the sterilization objects before entry into the sterilization chamber 10.

The reaction pressure inside the sterilization chamber 10 is maintained at a level lower than the atmospheric pressure during the sterilization process. At this pressure, the hydrogen peroxide vapor, which plays a crucial role in the sterilization, cannot easily penetrate into thin, long lumens, for example, the endoscopes with diameter of 1 mm or less and length of 50 cm or longer. Thus, an additional booster may be attached to each end of the lumen to inject the hydrogen peroxide vapor therethrough, bringing about faster and more reliable sterilization.

High frequency power from the power source 35 is applied to the cathode 33 of the sterilization chamber 10 under the control of the impedance matching circuit 37 and the impedance controller 36. Because of the high frequency power applied to the cathode 33 in the sterilization chamber 10, the high density plasma is generated between the cathode 33 and the anode 34 in the sterilization chamber 10. By adopting a pulsed high frequency power application manner where the power is applied intermittently, the high frequency power source 35, which is of a capacitively-coupled type, generates the high density plasma having a low temperature of 100° or lower.

Due to the high frequency power source 35 which is operated in the intermittent application manner, overheating of both the gas within the sterilization chamber 10 and the sterilization objects 11 is prevented.

With the high density plasma maintained in the plasma treatment module 31, if the vacuum pump 14 is being operated and the automatic pressure control valve 40 on the evacuating line 13 is opened, the hydrogen peroxide vapor within the sterilization chamber 10 is directed toward the plasma treatment module 31 along the exhaust line 13 and then released into the atmosphere via the vacuum pump 14.

While passing through the plasma generated in the plasma treatment module 31, the hydrogen peroxide vapor within the sterilization chamber 10 undergoes decomposition into water, hydrogen, and oxygen, which can be released into the air, as they are environmentally friendly and non-toxic. That is, the plasma functions to decompose the hydrogen peroxide vapor toxic to the body, into non-toxic water, oxygen and hydrogen, by virtue of its energy.

When the hydrogen peroxide vapor is perfectly evacuated from the sterilization chamber 10, the high frequency power source 35 is cut off. Then, the sterilization chamber 10 is ventilated to normal atmospheric pressure and the wrapped objects 11 thus sterilized are removed from the sterilization chamber 10.

In accordance with another aspect of the present invention, a sterilization method is provided, which is carried out in the same manner as described above, except that, after the sterilization chamber 10 is maintained in a predetermined vacuum state, the hydrogen peroxide vapor formed by heating the hydrogen peroxide solution 21 is injected at a pressure (1.033-1.36 kgf/cm$^2$) higher than the atmospheric pressure. Caution must be given to door lock and airtight maintenance because the inner pressure of the sterilization chamber 10 is higher than that in the atmosphere.

When the pressure of the sterilization chamber exceeds 1.36 kgf/cm$^2$, conventional plasma generators show some troubles in generating plasma.

In this sterilization method, hydrogen peroxide vapor is injected in abundance into the sterilization chamber 10 to the extent higher than the atmospheric pressure, so that the hydrogen peroxide vapor can strongly penetrate into the sterilization objects. Therefore, the sterilization method makes it possible to sterilize even thin, long lumens, such as endoscopes with diameter of 1 mm or less and length of 50 cm or greater, without the aid of boosters which are required at low pressures (lower than atmospheric pressure).

A better understanding of the present invention may be obtained through the following example which is set forth to illustrate, but is not to be construed as the limit of the present invention.

Example 1

Sterilization experiments were conducted by use of the plasma sterilization apparatus of the present invention and the results are given in Table 1.

*Bacillus stearothermophilus* (spore No. 2.0×10$^6$, ATCC7953) was used as a test microorganism, which is a biological indicator (BI) commercially available under the name "Cyclesure" produced by a company in the U.S. and used as a sterilization indicator for clinical instruments in many hospitals.

The BI was introduced into the plasma sterilization apparatus of the present invention, where plasma generation and sterilization are performed separately in different chambers, and a single-body type plasma sterilization apparatus, where plasma generation and sterilization occur in the single chamber. Sterilization was carried out at the optimal conditions for each sterilization apparatus (hydrogen peroxide vapor only, hydrogen peroxide plasma only). Thereafter, the collected BI samples were incubated at 55° C. for up to 7 days in an incubator and the color of the BI samples was analyzed. The results are shown in Table 1.

TABLE 1

| Sterilization Process | Test Results (Total 50 times) |
| --- | --- |
| Hydrogen Peroxide only | Pass 50*/Fail 0** |
| Hydrogen Peroxide Plasma only | Pass 0*/Fail 50** |

*BI samples display negative response (no color change)
**BI samples display positive response (color changed)

As shown in Table 1, in all of the experiments, which were carried out with only hydrogen peroxide vapor, the plasma sterilization apparatus of the present invention succeeded in sterilization, whereas none of the experiments carried out with only hydrogen peroxide plasma succeeded in sterilization. These results demonstrate that hydrogen peroxide vapor plays an essential role in the sterilization.

Example 2

When using the plasma treatment module-equipped sterilization apparatus of the present invention, residual levels of the hydrogen peroxide evacuated to the air from the sterilization chamber were measured and the results are given in Table 2.

In this regard, a residual peroxide-tester (Merck, 110011), capable of measuring residual levels of hydrogen peroxide (in ppm), was utilized to quantitatively analyze the hydrogen peroxide exhausted from the sterilization apparatus of the present invention during the sterilization.

The residual peroxide-tester was operated every 10 mins for the measurement of the residual levels of hydrogen peroxide. The tester was mounted on the back end of the vacuum pump from which the exhaust gas was released. Under optimal conditions, the residual level of the hydrogen peroxide exhausted in each step of the process is measured. After that, the colors of the samples obtained in the respective steps of the process were compared.

TABLE 2

| Processes | Test Results (ppm/10 rounds) | Features | Note |
|---|---|---|---|
| Evacuating (Vacuum) | 0 | Plasma always generated in all processes | $H_2O_2$ injection cut-off |
| Injection & Diffusion | 10 or less | | $H_2O_2$ injection initiated |
| Plasma treatment | 10 or less | | $H_2O_2$ injection maintained |
| Ventilating | 0 | | $H_2O_2$ injection cut-off |

As seen in Table 2, hydrogen peroxide vapor was released at 10 ppm or less at most, which demonstrated that most of the exhausted gas from the sterilization apparatus of the present invention was not hydrogen peroxide.

Example 3

Variation in the sterilization effect resulting from change in the sterilization pressure of the plasma treatment module-equipped sterilization apparatus of the present invention was tested and the results are given in Table 3.

In the experiment, the same microorganism sample as in Example 1 was used.

First, a couple of thin, long lumens, each $\phi 1$ mm or less in diameter and 200 cm in length, were prepared. The BI was inserted into each of the lumens. Then, the lumens were introduced into the sterilization chamber without booster. Sterilization experiments were carried out under the optimal condition, followed by culturing the BI samples taken from each of the lumens in an incubator at 55° C. for up to 7 days.

TABLE 3

| Reaction Gas | Reaction Pressure | Test Results (BI, 50 times) |
|---|---|---|
| Hydrogen Peroxide Vapor | 0.0163 kgf/cm$^2$ | Pass 0/Fail 50 |
| Hydrogen Peroxide Vapor | 1.0600 kgf/cm$^2$ | Pass 50/Fail 0 |

When the reaction pressure was as low as 0.0163 kgf/cm$^2$, the thin, long lumens, with diameter of 1 mm or less and length of 200 cm, were not sterilized at all. In contrast, sterilization was completely achieved at pressures as high as 1.0600 kgf/cm$^2$.

Taken together, the results of Table 3 lead to the conclusion that hydrogen peroxide vapor, which plays an essential role in the sterilization, can not penetrate into the depth of thin, long lumens $\phi 1$ mm or less with a length of 200 cm at a low reaction pressure, whereas high reaction pressure of hydrogen peroxide vapor can effectively penetrate through such lumens, thereby achieving perfect sterilization.

Example 4

Sterilization was made at reaction pressures higher and much lower than atmospheric pressure by use of the sterilization apparatus of the present invention. The results are given in Table 2.

To evaluate the sterilization capacity at various reaction pressures of the sterilization apparatus of the present invention, sterilization objects (suction catheters, Nelaton Catheters, operational scissors, stainless lumens, and balloon catheters) were introduced in sterilization pouches along with the same BI sample as in Examples 1 and 3. And then the prepared sterilization objects are introduced randomly into the sterilization chamber to the extent that the sterilization chamber was full (about 100% of filling capacity: 250 BI, regarded 100% of filling capacity in the case that the objects occupied the same volume with the total inner volume, 80 liters, of the sterilization chamber when it was completely empty). Then, sterilization was performed under the optimal conditions for the apparatus. Following completion of the sterilization, the BI samples collected from each pouch were incubated at 55° C. for up to 7 days in an incubator. The colors of the indicator samples were compared with the test results. (Refer to Table 4).

TABLE 4

| Reaction Gas | Reaction Pressure | Capacity (%) | Test Results (250 BI, 50 times) |
|---|---|---|---|
| $H_2O_2$ | 0.0163 kgf/cm$^2$ | 100 | Avg. pass 10/250 BI |
| $H_2O_2$ | 1.0600 kgf/cm$^2$ | 100 | Avg. pass 250/250 BI |

As apparent from the results of Table 4, the sterilization apparatus of the present invention completely sterilized only ten of the 250 BI introduced in pouches, at a low reaction pressure when the sterilization chamber was full (100% of filling capacity), whereas all of the tested specimens were perfectly sterilized at a reaction pressure higher than atmospheric pressure, even if the sterilization objects occupied the full volume of the sterilization chamber. These results lead to the conclusion that the sterilization apparatus of the present invention is not limited in terms of reaction chamber size and can achieve perfect sterilization even at the capacity of 100%.

INDUSTRIAL APPLICABILITY

As described above, the present invention provides a plasma treatment module-equipped sterilization apparatus and a sterilization method, in which only hydrogen peroxide vapor is used as a sterilizing agent to kill microorganisms present on articles, such as medical instruments and tools, and is decomposed into non-toxic materials, e.g., oxygen, hydrogen and water, while undergoing a reaction with plasma generated in the plasma treatment module.

Additionally, the present invention provides the advantage that thin, long lumens, such as endoscopes with diameter of $\phi 1$ mm or less and with a length of 50 cm or more, can be easily sterilized without the aid of boosters when hydrogen peroxide vapor is injected at a pressure higher than atmospheric pressure into the sterilization chamber.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A plasma treatment module-equipped sterilization apparatus, comprising: a sterilization chamber for receiving therein sterilization objects; a sterilizing agent feeding line, interconnected with the sterilization chamber, comprising a hydrogen peroxide solution, acting as a sterilizing agent, an injection heater for vaporizing the sterilizing agent by heating, and a mass flow controller for controlling the injection amount of the vaporized hydrogen peroxide solution; and a vacuum pump, connected to the sterilization chamber via an exhaust line, for exhausting air from the sterilization chamber to form a vacuum state, wherein a plasma treatment module is provided on the exhaust line to treat the vapor from the sterilization chamber with plasma while the vapor is passing through the plasma.

2. The plasma treatment module-equipped sterilization apparatus as set forth in claim 1, wherein the plasma treatment module comprises two electrodes, facing each other, as a cathode and an anode therein, and is connected to a plasma generator composed of a high frequency power source, an impedance matching controller and an impedance matching circuit.

3. A sterilization method utilizing the apparatus of claim 1, comprising the steps of: introducing sterilization objects into the sterilization chamber and closing the chamber; forming a desired pressure in the sterilization chamber by use of the vacuum pump, injecting hydrogen peroxide vapor into the sterilization chamber to a desired reaction pressure and keeping the sterilization objects in the hydrogen peroxide vapor for a desired period of time to achieve sterilization; and exhausting the hydrogen peroxide vapor from the sterilization chamber by means of the vacuum pump and decomposing the hydrogen peroxide vapor into oxygen, hydrogen and water in the plasma treatment module while the vapor is passing through plasma generated by the plasma treatment module.

4. The sterilization method as set forth in claim 3, wherein the hydrogen peroxide vapor is injected into the sterilization chamber at a pressure higher than atmospheric pressure.

5. A plasma treatment module-equipped sterilization apparatus, comprising: a sterilization chamber for receiving therein sterilization objects; a sterilizing agent feeding line, interconnected with the sterilization chamber, comprising a hydrogen peroxide solution, acting as a sterilizing agent, an injection heater for vaporizing the sterilizing agent by heating, and a mass flow controller for controlling the injection amount of the vaporized hydrogen peroxide solution; and a vacuum pump, connected to the sterilization chamber via an exhaust line, for exhausting air from the sterilization chamber to form a vacuum state, wherein a plasma treatment module is provided on the exhaust line at a location between the sterilization chamber and the vacuum pump to treat the vapor from the sterilization chamber with plasma while the vapor is passing through the plasma.

6. The plasma treatment module-equipped sterilization apparatus as set forth in claim 5, further comprising an automatic pressure control valve positioned on the exhaust line to control the internal pressure of the sterilization chamber and the plasma treatment module.

* * * * *